US006867187B2

(12) United States Patent
Clevenger et al.

(10) Patent No.: US 6,867,187 B2
(45) Date of Patent: Mar. 15, 2005

(54) COMPOSITION AND METHOD FOR MODULATING SOMATOLACTOGENIC FUNCTION

(75) Inventors: Charles V. Clevenger, Merion Station, PA (US); J. Bradford Kline, Blue Bell, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 137 days.

(21) Appl. No.: 10/029,079

(22) Filed: Dec. 21, 2001

(65) Prior Publication Data

US 2002/0119154 A1 Aug. 29, 2002

Related U.S. Application Data

(60) Provisional application No. 60/258,285, filed on Dec. 22, 2000.

(51) Int. Cl.⁷ ............................................. A61K 38/00
(52) U.S. Cl. ............................ 514/12; 514/2; 530/350; 530/399
(58) Field of Search ................. 514/2, 12; 530/350, 530/399

(56) References Cited

PUBLICATIONS

Amit et al., "Characterization of prolactin–and growth hormone–binding proteins in milk and their diversity among species", 1997 *Mol. Cell. Endrocrinol.* 130: 167–180.

Barnard et al., "The serum growth hormone binding protein:pregnant with possibilities", 1997 *J. Endocrinol* 153:1–14.

Baumann et al., A Specific Growth Hormone–Binding Protein in Human Plasma:Initial Characterization 1986 *J. Clin. Endocrinol. Metab.* 62:134–141.

Baumbach et al., "The growth hormone–binding protein in rat serum is an alternatively spliced form of the rat growth hormone receptor", 1989 *Genes Dev.* 3: 1199–1205.

Leav et al., "Prolactin Receptor Expression in the Developing Human Prostate and in Hyperplastic, Dysplastic, and Neoplastic Lesions", 1999 *Am. J. Path.* 154:863–870.

Leung et al., "Growth hormone receptor and serum binding protein:purification, cloning and expression", 1987 *Nature* 330:537–543.

Mercado et al., "A Growth Hormone–Prolactin–Binding Protein in Human Milk", 1994 *J. Clin. Endocrinol. Metab.* 79(6):1637–1641.

Peeters et al., "A Growth Hormone Binding Factor in the Serum of Pregnant Mice", 1977 *Endocrinology* 101:1164–1183.

Postel–Vinay et al., "Indentification of prolactin and growth hormone binding proteins in rabbit milk", 1991 *Proc. Natl. Acad. Sci. USA* 88:6687–6690.

Sotiropoulos et al., "Evidence for Generation of the Growth Hormone–Binding Protein Through Proteolysis of the Growth Hormone Membrane Receptor", 1993 *Endocrinology* 132(4):1863–1865.

Trivedi et al., "Release of Growth Hormone Binding Protein from IM–9 Lymphocytes by Endopeptidase is Dependent on Sulfydryl Group Inactivation", 1988 *Endocrinology* 123(5):2201–2206.

Walker et al., "Prolactin–immunoglobulin G complexes from human serum act as costimulatory ligands causing proliferation of malignant B lymphocytes" 1995 *Proc. Natl Acad. Sci. USA* 92:3278–3282.

Ymer et al., "Evidence for the specific binding of growth hormone to a receptor–like protein in rabbit serum", 1985 *Mol. Cell. Endocrinol.* 41:153–161.

*Primary Examiner*—Christopher Tate
*Assistant Examiner*—Roy Teller
(74) *Attorney, Agent, or Firm*—Licata & Tyrrell P.C.

(57) ABSTRACT

A human prolactin-binding protein and compositions and methods using this protein are provided.

2 Claims, 5 Drawing Sheets

A

IP: α-PRLr
IB: α-PRLr

B

C

COMPOSITION AND METHOD FOR MODULATING SOMATOLACTOGENIC FUNCTION

This application claims the benefit of priority from U.S. Provisional Application Ser. No. 60/258,285 filed Dec. 22, 2000.

This invention was supported in part by funds from the U.S. government (NIH Grant No. 2R01CA69294 and 1F32DK09727) and the U.S. government may therefore have certain rights in the invention.

BACKGROUND OF THE INVENTION

Prolactin and growth hormone receptors are members of the cytokine receptor superfamily. Both the prolactin receptor (PRLR) and growth hormone receptor (GHR) are single chain transmembrane proteins composed of an extracellular, transmembrane and intracellular domain. The hormones prolactin (PRL) and growth hormone (GH) exert their effects at the molecular level by inducing the homodimerization of their respective receptors, initiating the activation of receptor-associated kinases and signaling cascades.

Until the last few decades, it was believed that peptide hormones circulated freely, but experimental evidence has now proven otherwise. While PRL was found to associate with serum IgG, (Walker et al. 1995 Proc. Natl Acad. Sci. USA 92: 3278–3282) a GH-binding factor was initially identified in the serum of pregnant mice, (Peeters et al. 1977 Endocrinology 101: 1164–1183) and subsequently discovered in rabbit (Ymer et al. 1985 Mol. Cell. Endocrinol. 41: 153–161) and human sera. (Baumann et al. 1986 J. Clin. Endocrinol. Metab. 62: 134–141). With subsequent cloning of the GHR cDNA, a GH-binding protein (GHBP) was found to have amino acid sequence identity with the extracellular domain of the membrane-bound GHR. (Leung et al. 1987 Nature 330: 537–543) The GHBP is a 246 residue glycoprotein with a molecular weight of 50–60 kDA. The generation of GHRBP occurs via two separate mechanisms in mammals. In the mouse and rat, alternative splicing of a primary RNA transcript generates a truncated receptor in which the transmembrane domain is replaced by a short hydrophilic sequence (Smith et al. 3: 984–990; Baumbach et al. 1989 Genes Dev. 3: 1199–1205; Barnard et al. 1997 J. Endocrinol 153: 1–14). In other species, such as man and rabbits, a full length GHR is expressed, but GHBP is generated by proteolytic cleavage of the extracellular domain (Leung et al. 1987 Nature 330: 537–543; Trivedi et al. 1988 Endocrinology 123: 2201–2206; Sotiropoulos et al. 1993 Endocrinology 132: 1863–1865).

Although proteins in milk and serum have been found to interact with PRL, the identity of these species with the PRLR ECD had not been established. Evidence for these binding proteins in milk has been shown for man (Mercado et al. 1994 J. Clin. Endocrinol. Metab. 79: 1637–1641; Amit 1997 Mol. Cell. Endocrinol. 130: 167–180) as well as pigs, sheep and rabbits (Amit 1997 Mol. Cell. Endocrinol. 130: 167–180; Postel-Vinay et al. 1991 Proc. Natl. Acad. Sci. USA 88: 6687–6690). Even though the PRLR is highly homologous to the GHR, there was no clear evidence for a PRLP in mammalian serum.

A human prolactin-binding protein (hPRLBP) has now been identified in human serum homologous to the extracellular domain of the PRLR and a recombinant hPRLBP has been prepared. Based on its PRL binding ability, the rhPRLBP has been shown to inhibit PRL-induced proliferation of Nb2 This application claims the benefit of priority from

SUMMARY OF THE INVENTION

The present invention provides a human prolactin-binding protein and methods of its use for modulating somatolactogenic function.

Using both monoclonal and polyclonal antibodies generated against hPRL and the extracellular domain (ECD) of the human prolactin receptor (hPRLR), co-immunoprecipitation analyses of human serum and milk identified a 32 kDA hPRLBP. A measurable fraction of circulating PRL was associated with the hPRLBP. Studies showed that the hPRLBP antagonizes PRL action, inhibiting PRL-driven growth in a dose-dependent manner.

Accordingly, the present invention provides a method for modulating somatolactogenic function in an animal comprising administering an effective amount of isolated or recombinant hPRLBP.

A method of inhibiting the proliferation of Nb2 cells comprising contacting Nb2 cells with the hPRLBP is also provided.

The hPRLBP and a composition comprising the hPRLBP are also an object of the present invention.

Another object of the invention is methods and reagents for diagnosing diseases associated with somatolactogenic functions in patients by detecting the hPRLBP in patients.

Pre-cleared sera samples and breast milk were immunoprecipitated with α-PRLR antiserum and subjected to immunoblot analysis with a 1:1000 dilution of anti-PRLR. B) Quantitation of PRLBP in the sera of both sexes. Bands from FIG. 3A were analyzed by densitometry against known quantities of recombinant PRLBP to quantitate the amounts of PRLBP found in serum. Males, 15.3±1.3 ng/ml; females, 13.4±0.8 ng/ml (mean±S.E.M.).

Figure 4:
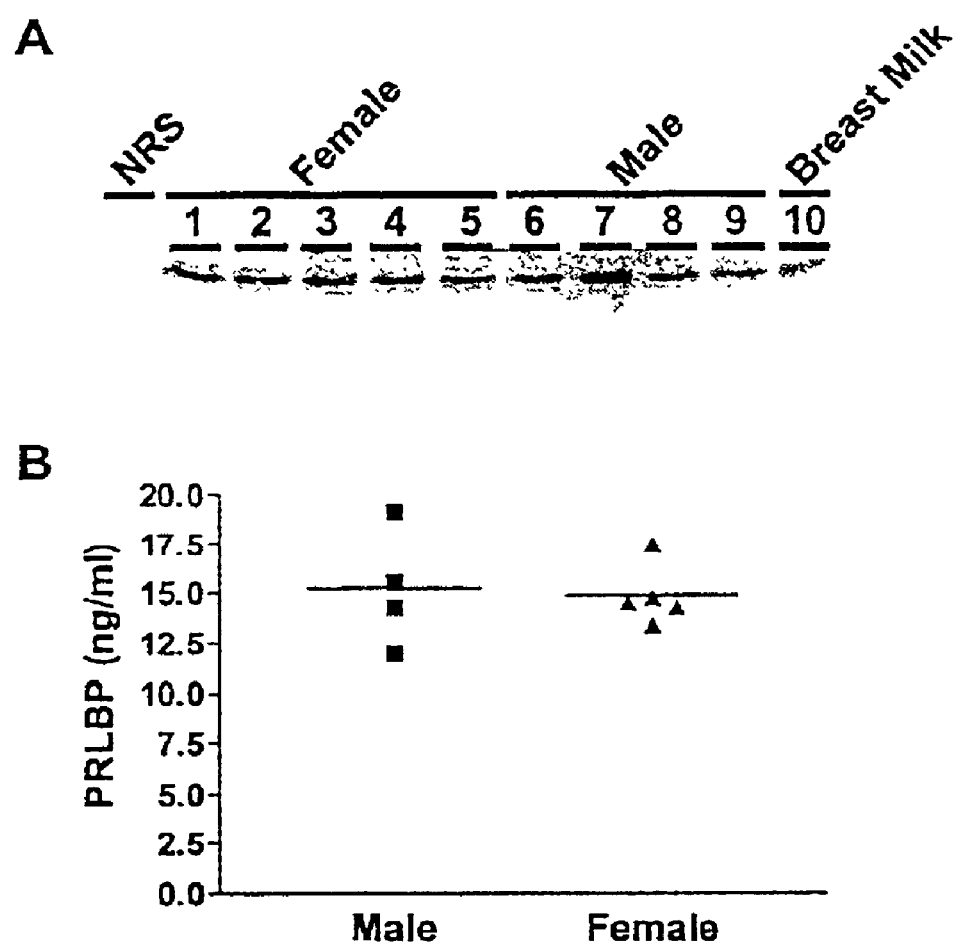

FIG. 4 shows the biochemical characterization of the PRLBP. A) PRLBP is not glycosylated. Pre-cleared serum was immunoprecipitated with anti-PRLR antiserum and the immunoprecipitate was washed and incubated with or without 10 units PNGase F in buffer for 8 hours at 37° C. Samples were immunoblotted in parallel with recombinant PRLBP and probed with a 1:1000 dilution of anti-PRLR mAb. B) Proteolytic analysis of serum PRLBP versus PRLR ECD. Serum was immunoprecipitated with anti-PRLR antiserum as described above, electrophoresed, and stained with Coomassie brilliant blue. Excised bands were digested with Asp-N and Lys-C and peptide fragments separated on a 20% Tris-Tricine PAGE gel. Bands were visualized using the Silver-Stain Plus kit (Bio-Rad) and scanned for densitometric analysis. Recombinant PRLR ECD served as a positive control, GST as a negative control. Representative of one of two experiments. C) MALDI-MS identification of the hPRLBP. Serum was immunoprecipitated with protein A beads covalently linked to anti-PRLr antibodies. Eluted hPRLBP was electrophoresed and stained with Silver Stain Plus (Bio-Rad). Excised bands were digested with trypsin and subjected to MALDI-MS. Two peptides corresponding to the ECD of the human PRLr are indicated.

Figure 5:
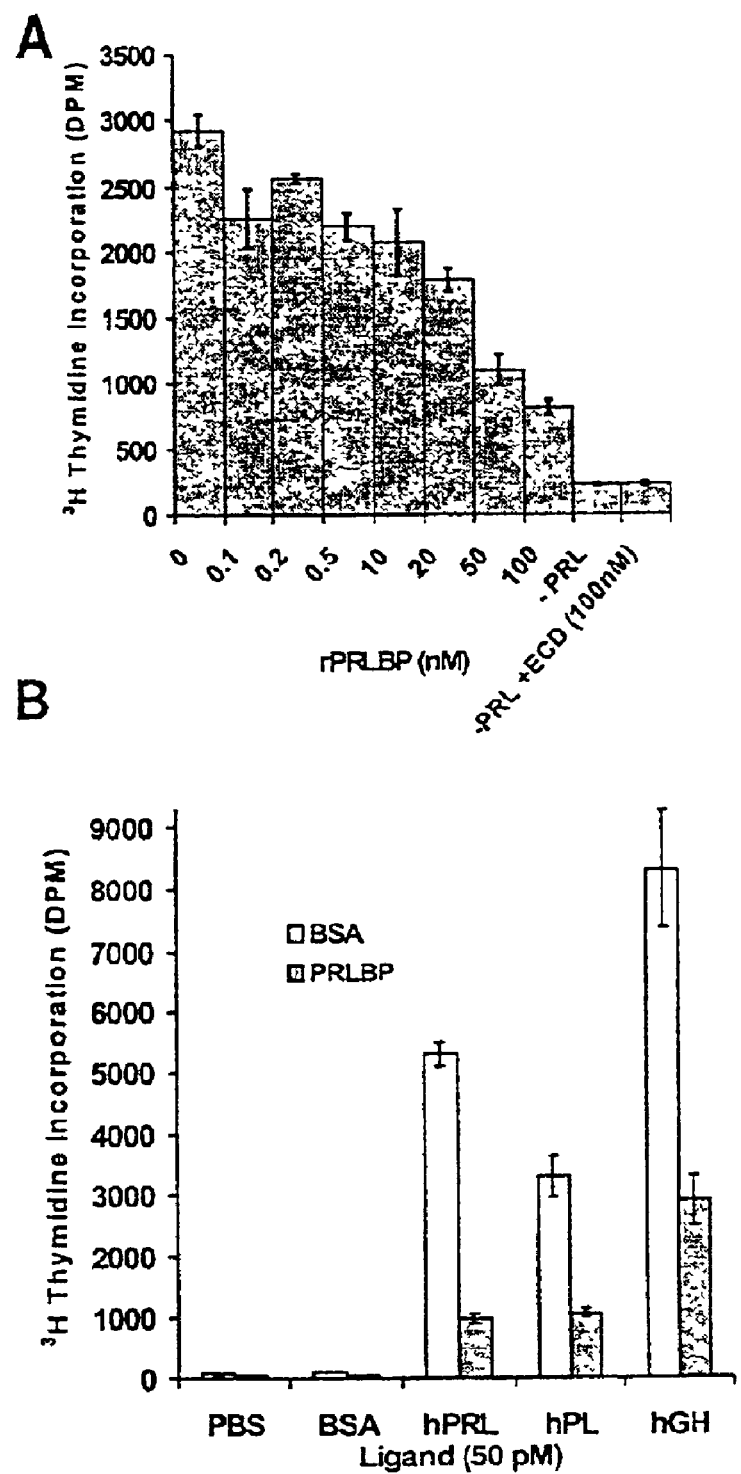

FIG. 5 shows the effect of rhPRLBP on the proliferation of Nb2 lymphoma cells. A) rhPRLBP blocks hPRL-induced Nb2 cell proliferation in a dose-dependent manner. $1 \times 10^4$ cells were plated overnight in DMEM/ITS+supplemented with 50 pM hPRL and increasing concentrations of hPRLBP. Proliferation was assessed by tritiated thymidine uptake. Results are mean DPM of triplicate wells±S.E.M. B) rhPRLBP blocks Nb2 cell proliferation induced by hPL and hGH. $1 \times 10^4$ cells were plated overnight in DMEM/ITS+ supplemented with 50 pM hPRL, hPL, or hGH in conjunction with 100 nM rhPRLBP or 100 nM BSA. Proliferation was assessed by tritiated thymidine uptake. Results are mean DPM of triplicate wells±S.E.M.

DETAILED DESCRIPTION OF THE INVENTION

The present invention provides a human prolactin-binding protein (PRLBP). A soluble PRLBP was isolated from human plasma. Using a high avidity anti-PRLR anti-serum, a protein was immunoprecipitated from human plasma which was recognized by an anti-PRLR monoclonal antibody by Western analysis. This serum PRLBP had a molecular mass of 32 kDa and was not glycosylated based on the inability of a glycosidase to affect its electrophoretic mobility. Using proteolytic digestion, the homology of the PRLBP with the PRLR extracellular domain was confirmed. The immunoprecipitated PRLBP was digested with trypsin and chymotrypsin and the peptide fragments analyzed by Tris-Tricine PAGE as compared to digested recombinant PRLR extracellular domain. Both proteins exhibited identical peptide fingerprints with both digestions, further supporting the correlation between the PRLBP and the ECD of the PRLR. The digestion pattern also correlated with the computer-predicted digestion of PRLR ECD and was not consistent with the predicted digestion of the GHBP or the Fab portion of the IgG heavy chain. Given the existing precedent with the naming of the GHBP, the serum PRLR ECD is identified as PRLBP. The PRLBP was present in the sera of both males and females at comparable levels. The presence of PRLBP in vivo may serve to maintain a reservoir of PRL in the circulation, providing a releasable pool of free hormone in times of diminishing supply.

The ligand characteristics of the PRLBP were determined. The PRLBP was found associated with both PRL and GH in human serum and approximately 36% of plasma PRL was found associated with PRLBP in a single donor. Further, since hPRLBP was capable of binding PRL, the effect on Nb2 cellular proliferation was studied. The effect of purified recombinant PRLBP on the biological activity of hPRL using the rat Nb2–11c lymphoma cell proliferation assay was evaluated. As increasing concentrations of PRLBP were added, a three-fold reduction in cell proliferation was found. This was a consequence of the sequestering of PRL by PRLBP rather than protein toxicity, as PRLBP itself was not toxic the cells. Therefore, the overall decrease in proliferation can be attributed to the PRLBP competing with cell surface receptors for ligand, effectively reducing the amount of PRL bound to surface receptors and decreasing receptor homodimerization.

Figure 1:
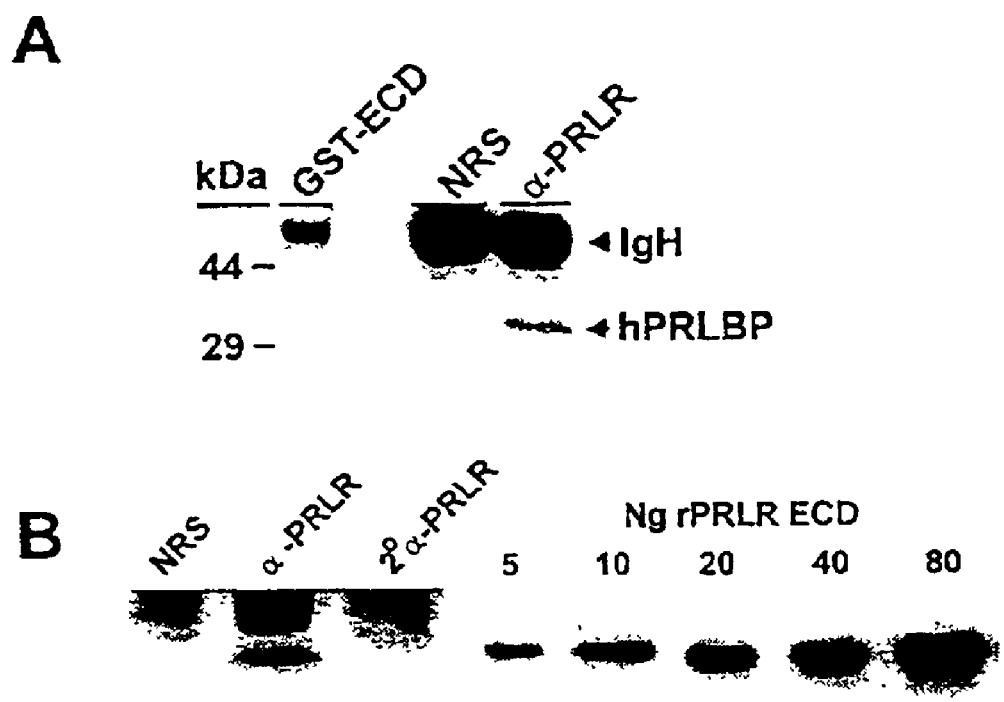
FIG. 1 depicts a gel showing PRLBP is expressed in human serum. A) Immunoprecipitation of PRLBP from serum. Samples (1 ml) of pre-cleared serum were immunoprecipitated 5 μl of normal rabbit serum (NRS) or anti-PRLR antiserum overnight at 4° C. After washing, precipitates were analyzed by immunoblot using anti-PRLR mAb (1:1000). An *E.coli* expressed fusion of the hPRLR ECD to GST (GST-ECD) served as a positive control for antibody specificity. Representative of one of three experiments. B) Quantitation of PRLBP in human serum. PRLBP was immunoprecipitated from serum as in FIG. 1A. To ensure complete precipitation of PRLBP, serum was immunoprecipitated a second time (2°α-PRLR). Immunoprecipitates were electrophoresed in parallel with known quantities of recombinant PRLBP. Amounts of PRLBP in serum were calculated based on densitometry quantitation of standards. Representative of one of three experiments.

Expression of a PRLBP in human serum. Until the present invention, no protein with homology to the PRLR ECD had been found in sera, and the existence of such a protein in milk had been only indirectly implicated (Mercado et al. 1994. J. Clin. Endocrinol. Metab. 79:1637–1641; Amit et al. 1997. Mol. Cell Endocrinol. 130:167–180; Postel-Vinay et al. 1991. Proc. Natl. Acad. Sci. USA 88:6687–6690). Using a recently characterized anti-PRLR antiserum (Leav et al. 1999. Am. J. Path. 154:863–870) in conjunction with monoclonal antibody, a bonafide PRLBP (i.e. the free PRLR ECD) was identified in human serum. Human serum extensively pre-cleared of immunoglobulin was immunoprecipitated with antiserum raised against the extracellular domain of the PRLR. Immunoblot analysis of this precipitate with a specific anti-PRLR mAb showed that the immunoprecipitate contained an immunoreactive protein corresponding to the approximate molecular weight of the extracellular domain of the human PRLR (FIG. 1A). This band was absent in the control lane using normal rabbit serum for the immunoprecipitation, illustrating the immunospecificity of the anti-PRLR antiserum. To quantitate the amount of PRLBP in the donor serum, the immunoprecipitation was repeated and immunocomplexes were electrophoresed in conjunction with known quantities of recombinant PRLR extracellular domain (rPRLR ECD) (FIG. 1B). To ensure complete precipitation of PRLBP, the serum was used in a second round of immunoprecipitation (FIG. 1B, lane 3), revealing that the first immunoprecipitation had concentrated nearly all of the serum PRLBP. By comparison to the rPRLR ECD standards, it was determined that the donor had 13.8±1.4 ng (mean±S.E.M.) PRLBP per ml of serum.

Figure 2:
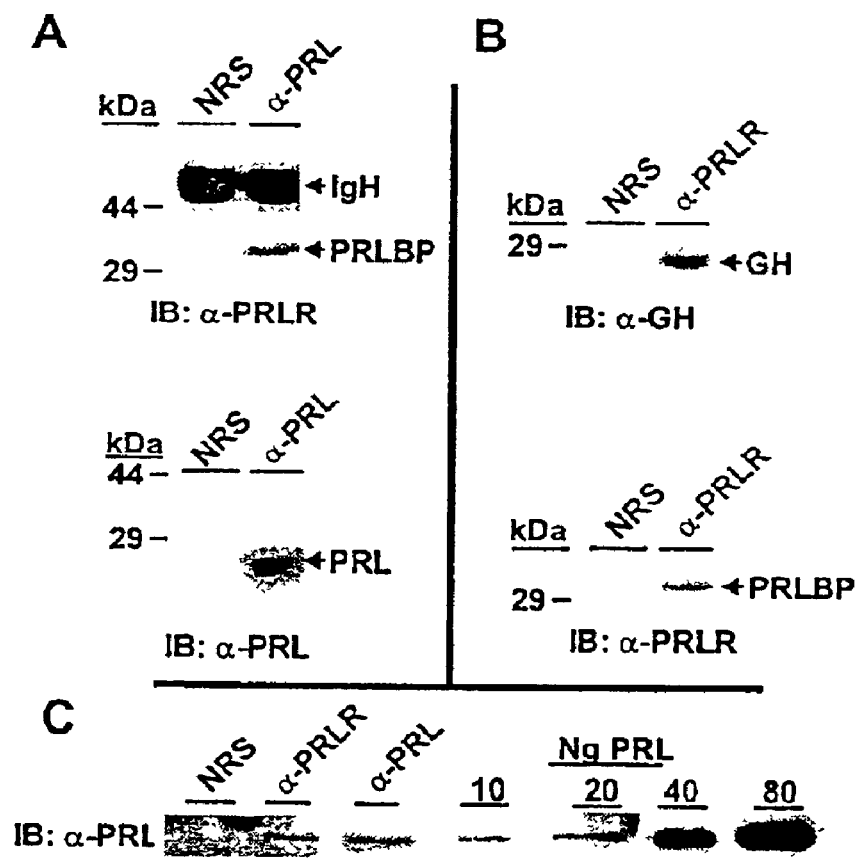
FIG. 2 shows how PRLBP associates with PRL and GH in human serum. A) Association of serum PRL with PRLBP. Pre-cleared serum was immunoprecipitated with normal rabbit serum (NRS) or goat anti-PRL antiserum (α-PRL). Immunoprecipitates were subjected to immunoblot analysis with α-PRLR mAb (top panel). The blot was stripped and reprobed with a 1:1000 dilution of α-PRL antiserum to ensure the immunoreactive specificity of the antiserum (bottom panel). Representative of one of three experiments. B) Association of serum GH with PRLBP. Pre-cleared serum was immunoprecipitated with normal rabbit serum (NRS) or anti-PRLR antiserum (α-PRLR) and immunoprecipitates subjected to immunoblot analysis with a 1:1000 dilution of α-PRLR mAb (bottom panel). Representative of one of two experiments. C) Quantitation of PRL bound to PRLBP in serum. Pre-cleared serum samples (1 ml) were immunoprecipitated overnight with anti-PRLR, anti-PRL, or normal rabbit serum (NRS). Immunoprecipitates were electrophoresed in conjunction with known quantities of recombinant hPRL to determine the percentage of serum PRL complexed with PRLBP. Representative of one of two experiments.

Binding of Serum PRLBP . Unlike any other species, hGH has the capacity to bind both the PRLR and GHR. Previous studies showed that a milk PRL-interacting protein and GHBP both are capable of binding radiolabeled hGH (Postal-Vinay. 1991. Proc. Natl. Acad. Sci. USA 88:6687–6690). To determine if there was an association between hPRL or hGH and PRLBP in human serum, coimmunoprecipitations were performed, as shown in the top panel of FIG. 2A, anti-PRLR immunoblot analysis of anti-PRL immunoprecipitates revealed the association of the PRLBP with serum PRL. Stripping and reprobing the blot with anti-PRL antibody shows the immunoprecipitating antiserum was specific for PRL (FIG. 2A, bottom panel). As shown in FIG. 2B, anti-GH immunoblot analysis of anti-PRLR immunoprecipitates revealed that hGH was also bound to the PRLBP. To quantitate the amount of serum PRL complexed with PRLBP, immunoprecipitations were performed using anti-PRLR and anti-PRL antisera, followed by immunoblotting with anti-PRL antiserum in conjunction with known concentrations of a PRL standard. As shown in FIG. 2C, 28 ng of PRL were found in 1 ml of a donor's serum, of which 10 ng or 36% coimmunoprecipitated with PRLBP as determined by known quantities of PRL electrophoresed in parallel. By similar methods, the amount of serum GH coimmunoprecipitating with PRLBP was analyzed. In this donor's serum, 2.6 ng of the 5 ng GH found in 1 ml of serum associated with PRLBP.

To further investigate the PRL binding properties of the PRLBP, a recombinant form of the PRLBP was generated in *E.coli* for subsequent analysis by surface plasmon resonance. Using various concentrations of rPRLBP, the dissociation constant ($K_d$) of binding site I was measured at 13.4 nM.

Figure 3:
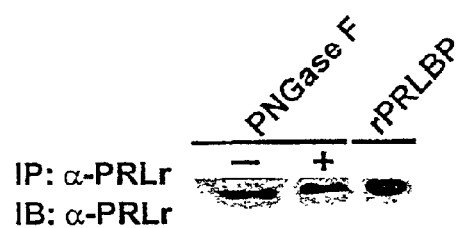
FIG. 3 shows PRLBP is expressed in the sera of both males and females. A) Immunoblot of serum samples.
Figure 3:
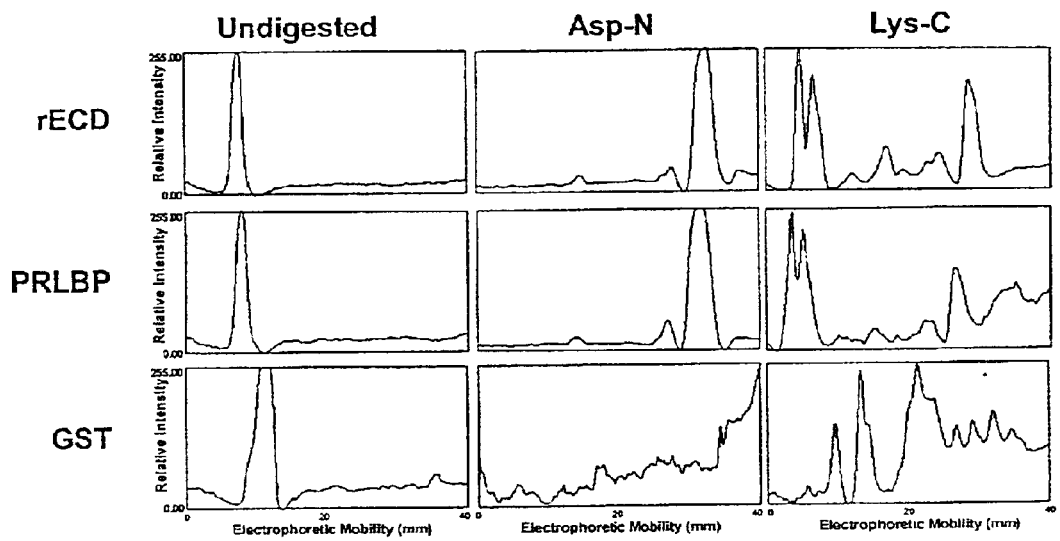
Figure 3:
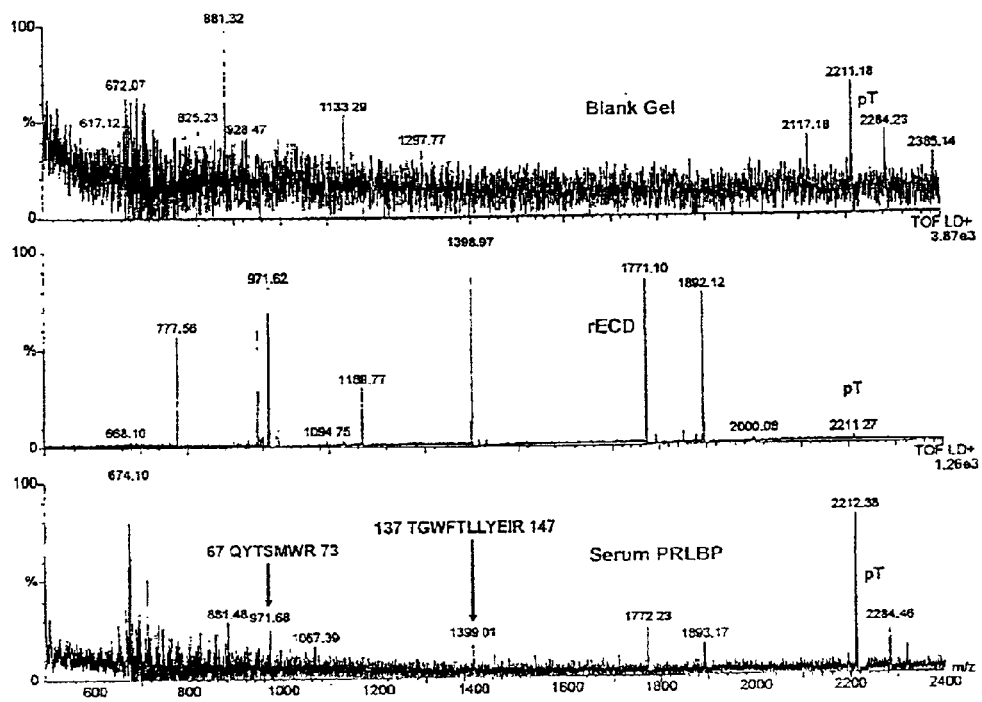

Both sexes have comparable levels of serum PRLBP. Since the previous experiments utilized the serum of a single, non-lactating female donor, the variation in the levels of PRLBP observed between the sexes was examined. This was accomplished by anti-PRLR immunoprecipitation analysis of donor serum and milk. As shown in FIG. 3, there was no significant difference in the amounts of PRLBP found in the sera of non-pregnant, non-lactating females (lanes 1 to 5) and males (lanes 6 to 9), with respective levels averaging 15.3±1.3 ng/ml versus 13.4+0.8 ng/ml PRLBP. No significant difference was found in the amounts of PRLBP found in the sera of these women as compared to sera from 24 hour post-partum mothers. Additionally, PRLBP was found in the breast milk of a lactating mother (FIG. 3A, lane 10), although at somewhat lower levels than in serum.

Biochemical identification of the PRLBP. The PRLR is known to be highly glycosylated on the asparagine residues of its extracellular domain. To determine if the PRLBP was glycosylated to a similar degree, immunoprecipitated PRLBP was treated with the general deglycosidase PNGaseF and then electrophoresed along with recombinant PRLBP expressed in *E. coli* (FIG. 4A). No shift in electrophoretic mobility was observed upon PNGase F treatment, suggesting serum PRLBP was not glycosylated and had the same apparent molecular weight as the recombinant form of the PRL ECD (32 kDa). Although two antibodies generated against the extracellular domain of the PRLR were immunoreactive against serum and milk PRLBP (see FIGS. 1 and 2), it could not be entirely ruled out that this was due to cross-reactivity to a highly homologous protein. Attempts at N-terminal amino acid sequencing however were non-informative, possibly due to a blocked N-terminus. Therefore, serum PRLBP was excised from an SDS-PAGE gel and subjected to protease digestion with Asp-N or Lys-C (FIG. 4B). As a positive control, recombinant PRLR ECD was digested in parallel. GST digestion served as a negative control. The peptide fragments resulting from the digestion of serum PRLBP showed an electrophoretic profile highly similar to the PRLR ECD (FIG. 4B, Row 1 vs. Row 2). In contrast, the pattern differed from that of GST (FIG. 4, Row 1 vs. Row 3), suggesting the PRLBP was indeed homologous to the extracellular domain of the PRLR. To confirm this observation, MALDI-MS was performed on PRLBP immunoprecipitated from serum as compared to recombinant human PRLBP. Four peptides with masses of 971, 1399, 1772 and 1893 correlated between the serum PRLBP and the positive control of rPRLr ECD (FIG. 4C, middle vs. bottom panel). Mass-database searching revealed homology to the PRLr ECD and two peaks corresponded to tryptic fragments of this region (FIG. 4C, bottom panel arrows). As the sequences of these tryptic fragments are unique to the hPRLR (as assessed by protein database scan), identity of the PRLBP to the PRLR ECD is established.

Inhibition of the Proliferation of Nb2 cells Stimulated with human PRL. As the GHBP can modulate the activity of GH, the effect of purified recombinant PRLBP on the biological activity of hPRL using the rat Nb2–11C lymphoma cell proliferation assay (FIG. 5) was evaluated. As increasing concentrations of PRLBP were added, a threefold reduction in cell proliferation was noted (FIG. 5A). Importantly, the PRLBP by itself was not toxic to cells. Therefore, the overall decrease in proliferation could be attributed to the PRLBP competing with cell surface receptors for ligand. This competition also extended to other members of the somatolactogenic family of ligands. As the control protein BSA was observed to have no positive or negative effect on PRL-induced proliferation, the effects of coincubation of BSA or PRLBP with other somatolactogenic hormones on Nb2 cell proliferation were compared. The inclusion of PRLBP into the medium of either PL- or GH-stimulated Nb2 cells was found to decrease ligand-induced cell proliferation, an effect not observed for BSA (FIG. 5B).

The present invention also relates to methods and compositions for modulating somatolactogenic functions using human prolactin-binding protein (hPRLBP). The rhPRLBP of the present invention comprises an amino acid sequence of SEQ ID No. 3. The nucleic acid sequence encoding the hPRLBP comprises SEQ ID NO. 4.

In one embodiment of the present invention, a composition comprising the hPRLBP in a pharmaceutically acceptable vehicle can be administered to a cell or an animal. Compositions comprising the hPRLBP can be used in the treatment of breast and prostate cancer, and in the treatment of conditions associated with excess PRL or GH such as pituitary adenomas which can lead to hyperprolactinemia or gigantism/acromegaly.

Appropriate doses of the hPRLBP can be administered to cells or animals and can be determined in accordance with well known techniques, such as cell culture experiments described herein. Determination of effective doses from such data is performed routinely by those of skill in the art. The hPRLBP or a composition thereof can be administered intravenously or intramuscularly. When used to augment somatolactogenic function, it is preferred that the dosage selected result in a serum concentration level similar to normal healthy individuals. To inhibit somatolactogenic function in an animal, a dose is selected to result in higher serum concentrations.

The present invention also related to a method and reagent for use in diagnosing diseases associated with abnormal somatolactogenic functions. The level of the hPRLBP of the invention is obtained from a biological sample such as serum or milk. In one embodiment, the levels are determined using an antibody, as described in the following examples. The level determined are compared with levels in normal individuals. Levels which are lower than levels in normal individuals are indicative of disease or conditions wherein somatolactogenic function must be augmented. Levels which are higher than in normal individuals are indicative of conditions or diseases wherein somatolactogenic function must be inhibited.

The invention is further described by the following, non-limiting examples.

EXAMPLES

Example 1

Sera and Milk Samples

Human sera was obtained from healthy male and female adult donors. Aliquots were stored at −80° C. and clarified by centrifugation at 12,000 g for 30 minutes before use. Human milk was obtained from a lactating mother and defatted by centrifugation. Infranatant was collected by avoiding the upper lipid layer as well as any sediment and stored at −80° C.

Example 2

Expression of Recombinant Human Prolactin Binding Protein (rhPRLBP)

A cDNA fragment of the human long PRLR was amplified by polymerase chain reaction with primers homologous to the mature from of the extracellular domain. The primers PRLR-1 (5'-CGAATTCCAGTTACCTCCTGGA-3'; SEQ ID NO: 1) and PRLR-211'(5'-GCTCGAGTCATGTATCATTCTGGT-3'; SEQ ID NO: 2) were used in the 50 µL amplification reaction with 50 ng of DNA template, 5 µL 10×PCR buffer, 3 µL of 25 mM $MgCl_2$, 1 µL of 10 mM dNTP mix, and 5 U of Taq polymerase (Life Technologies, Inc., Grand Island, N.Y.). After a 2 minute incubation at 94° C., the mixture was amplified for 30 cycles of 94° C. for 30 seconds, 47° C. for 30 seconds and 72° C. for 30 seconds. It was then extended at 72° C. for 2 minutes. The amplified fragment was purified and concentrated by phenol/chloroform extraction followed by ethanol precipitation. The pellet was resuspended in 40 µL of $dH_2O$ and 10 µL was digested with EcoRI and XhoI restriction enzymes and ligated into the corresponding restriction sites of pGEX4T-1 (Amersham Pharmacia Biotech, Piscataway, N.J.). The clone was subsequently checked for amplification errors by dideoxynucleotice sequencing. The resulting glutathione-S-transferase/extracellular domain fusion (GST-ECD) was expressed as per the manufacturer's instructions. Briefly, a 1 liter culture of E. coli transformant was grown to mid-log phase and induced with 0.1 mM IPTG for 4 hours. Pelleted cells were suspended in 20 ml of 10 mM EDTA and 10 mM Tris-HCI, pH 8.0 in the presence of 0.5 mg/ml lysozyme. Purification and solubilization of refolded GST-ECD was then carried out in accordance with well known methods. For purification of bioreactive recombinant human PRLBP (rhPRLBP), 1 ml of refolded GST-ECD preparation was incubated with 300 µL of glutathione beads for 30 minutes at 40° C. After washing the beads three times with PBS, protein was eluted in 300 µL PBS containing 10 mM reduced glutathione. Thrombin protease (10 U, Amersham Pharmacia Biotech) was added to the elution at room temperature for 18 hours. The digested protein solution was dialyzed overnight in 4 liters PBS and cleared of GST protein by three incubations with fresh glutathione beads. The purified rhPRLBP was electrophoresed on a 12% SDS-PAGE and stained with Coomassie blue to ensure the complete removal of GST protein, as well as undigested fusion protein. The sample was incubated for 1 hour with polymyxin beads to remove residual LPS, then filter sterilized, aliquoted and flash frozen.

Example 3

Immunoprecipitation of PRLBP and from Serum and Milk

Sera and milk samples (1 ml) were throughly pre-cleared of endogenous immunoglobulin by repeated overnight incubation with 300 µL of a protein A/G bead mixture. Precleared samples were then incubated overnight at 40° C. with 5 µL of rabbit anti-PRLR antiserum. As a negative control, an equal aliquot of serum was incubated with 5 µL normal rabbit serum. Immune complexes were then precipitated by the addition of 50 µL protein A beads for 30 minutes at 40° C. After three washes with lysis buffer (20 mM Tris-HCl, pH 7.5, 150 mM NaCl, 2 mM EDTA, 1% TRITON X-100, 1 mM pmsf, 1 mM and 1 ug/ml $Na_3VO_4$ aprotinin, pepstatin and leupeptin), the beads were suspended in 20 µL Laemmli buffer with mercaptoethanol and boiled. For immunoprecipitation of serum PRL, samples were treated in a similar manner except 5 µL of goat anti-PRL antiserum (Santa Cruz Biotechnology, Inc., Santa Cruz, Calif.) and 50 µL protein G beads were used. For co-immunoprecipitation of growth hormone with PRLBP, samples were immunoprecipitated with 5µL of rabbit anti-PRL antiserum plus 50 µL protein A beads, washed three times and suspended in Laemmli buffer.

Example 4

Immunoblot Analysis

Immune complexes were resolved by electrophoresis through a 12% SDS-polyacrylamide gel and transferred to PVDF membrane (BioRad Laboratories, Hercules, Calif.). Nonspecific binding was blocked with 5% milk in PBS/Tween 20. Antigens were labeled with 1:1000 dilutions of primary antibodies and 1:2500 dilutions of horseradish peroxidase coupled antibodies. Antigen-antibodies complexes were visualized by enhanced chemiluminescence (Amersham Pharmacia Biotech). The anti-PRLR antibody against human PRLR ECD was provided by Genzyme (Cambridge, Mass.). Rabbit anti-growth hormone antiserum was obtained from the NIDDK.

Example 5

Quantitation of Serum PRLBP, PRL and GH

To assess the quantities of PRLBP, PRL and GH found in sera, immune complexes were electrophoreses in parallel with known quantities of recombinant hPRLBP, hPRL or hGH. Visualized bands were then scanned and signal intensities were obtained using ImageQuaNT densitometry software (Molecular Dynamics, Inc. Sunnyvale, Calif.). This data was used to generate a concentration/intensity curve to quantitate unknown amounts of PRLBP, PRL or GH. Statistical analysis were performed using GraphPad Prism version 3.0 for Windows (GraphPad Software, San Diego, Calif.).

Example 6

Deglycosylation of Serum PRLBP.

PRLBP was immunoprecipitated with 5 µl of anti-PRLR antiserum and 50 µl protein A beads. Immune complexes were washed three times with lysis buffer, followed by three washes with 50 mM sodium phosphate, pH 7.5. Pellets were resuspended in 40 µl 50 mM sodium phosphate with or without 10 units of PNGase F (Sigma-Aldrich, St. Louis, Mo.) and incubated 8 hours at 37° C. Samples were washed once more with lysis buffer, resuspended in 40 µl Laemmli buffer and boiled. The treated and untreated samples were electrophoresed in parallel with 30 ng of recombinant PRLBP on a 12% SDS-PAGE gel. This served as a control for the electrophoretic mobility of nonglycosylated PRLBP on a reducing gel. Samples were transferred to PVDF and blotted with anti-PRLR monoclonal antibody.

Example 7 in Gel Protease Digestion of PRLBP

Pre-cleared serum (3 ml) was immunoprecipitated with 15 µL anti-PRLR antiserum, electrophoresed and stained with Coomassie brilliant blue (Bio-Rad, Inc., Hercules, Calif.). After extensive destaining with 45% methanol/10% acetic acid, the gel was washed with distilled water with several changes. The bands corresponding to the PRLBP were excised with a razor blade and suspended in 0.1 ml 100 mM ammonium carbonate. Asp-N or Lys-C protease (Sigma-Aldrich) was added (1:25 weight:weight) and the mixture thoroughly macerated with an Eppendorf pestle. After overnight digestion at 37° C., peptide fragments were separated from the gel pieces by centrifugation for 5 minutes at 2,000×g through a low-protein-binding microfilterfuge tube. Tricine sample buffer was added to the samples, boiled for 2 minutes and separated on a 20% TRIS-Tricine PAGE gel. Bands were visualized using the Silver-Stain Plus kit (Bio-Rad) in accordance with manufacturer's instructions. Predicted proteolytic maps were generated with the ExPASy Server tool PeptideMass.

Example 8

Mass Spectrometry

To isolate pure PRLBP from serum, covalently coupled anti-PRLr beads were generated for immunoprecipitation. Briefly, 200 µl affinity purified anti-PRLr antiserum was coupled to 100 µl protein A beads for 1 hour at room temperature. Beads were washed two times with 10 volumes of 0.2 M sodium borate (pH 9.0) and resuspended in 10 volumes 0.2 M sodium borate/20 mM dimethylpimelimidate (pH 9.0) for 30 minutes at room temperature. Beads were washed in 0.2 M ethanolamine (pH 8.0) and then incubated for 2 hours at room temperature in 0.2 M ethanolamine. The covalently coupled anti-PRLr beads were washed three times in PBS and mixed with 10 ml pre-cleared human serum overnight at 40° C. The beads were then washed three times in 10 mM phosphate buffer (pH 6.8) and bound protein was eluted in 5 M LiCl/10 mM phosphate buffer (pH 7.2). Sample was mixed with Laemmli buffer, boiled, and electrophoresed on a 10% SDS-PAGE gel. The gel was stained with Silver Stain Plus (Bio-Rad) and the band corresponding to the PRLBP excised for mass spectrometry. Samples corresponding to a plain gel slice and rhPRLBP were excised for use as negative and positive controls, respectively. The gel slices were subject to in-gel tryptic digestion by rehydrating with 200 ng sequencing grade trypsin (Promega, Madison, Wis.). Extractable tryptic peptides were subjected to MALDI-MS analysis using a paracrystalline film matrix method for desalting the extracts. Monoisotopic Mass Lists for the samples were generated and submitted for mass database searching using the Profound algorithm (Rockefeller University, New York, N.Y.).

Example 9

Inhibition of Nb2 Lymphoma Cell Proliferation with Recombinant PRLBP

Nb2–11 cells were maintained in Fishers medium supplemented with 10% FCS, 10% horse serum, 1 mM L-glutamine, 100 U penicillin, 10 ug streptomycin and 0.1 mm betamercaptoethanol. To assess the ability of recombinant hPRLBP to inhibit PRL-induced cellular proliferation, $1 \times 10^4$ Nb2 cells were aliquoted in triplicate wells in medium consisting of DMEM (Life Technologies, Inc.) supplemented with sodium selenide, linoleic acid, insulin and transferrin (ITS+; Calbiochem, Bedford, Mass.) in the presence or absence of 50 pM hPRL. Increasing concentrations (0–100 nM) of recombinant hPRLBP were simultaneously added to the wells. After overnight culture, cells were pulsed with 1 uCi of [$^3$H] thymidine at 37° C. for 4 hours. Incorporation of radiolabel was determined by scintillography of the harvested washed cells.

What is claimed:

1. An isolated human prolactin-binding protein wherein said human prolactin binding protein is produced recombinantly and has a sequence comprising SEQ ID NO: 3.

2. A composition comprising the prolactin-binding protein of claim 1 and a pharmaceutically acceptable vehicle.

* * * * *

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
cgaattccag ttacctcctg ga                                       22

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
gctcgagtca tgtatcattc tggt                                     24

<210> SEQ ID NO 3

```
<211> LENGTH: 210
<212> TYPE: PRT
<213> ORGANISM: Homo sapien

<400> SEQUENCE: 3

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Gln Met Gly Ser Ser Phe
            100                 105                 110

Ser Asp Glu Leu Tyr Val Asp Val Thr Tyr Ile Val Gln Pro Asp Pro
        115                 120                 125

Pro Leu Glu Leu Ala Val Glu Val Lys Gln Pro Glu Asp Arg Lys Pro
    130                 135                 140

Tyr Leu Trp Ile Lys Trp Ser Pro Pro Thr Leu Ile Asp Leu Lys Thr
145                 150                 155                 160

Gly Trp Phe Thr Leu Leu Tyr Glu Ile Arg Leu Lys Pro Glu Lys Ala
                165                 170                 175

Ala Glu Trp Glu Ile His Phe Ala Gly Gln Gln Thr Glu Phe Lys Ile
            180                 185                 190

Leu Ser Leu His Pro Gly Gln Lys Tyr Leu Val Gln Val Arg Cys Lys
        195                 200                 205

Pro Asp
    210

<210> SEQ ID NO 4
<211> LENGTH: 633
<212> TYPE: DNA
<213> ORGANISM: Homo sapien

<400> SEQUENCE: 4
atgaaggaaa atgtggcatc tgcaaccgtt ttcactctgc tacttttct  caacacctgc      60 cttctgaatg gacagttacc tcctggaaaa cctgagatct ttaaatgtcg ttctcccaat     120
aaggaaacat tcacctgctg gtggaggcct gggacagatg gaggacttcc taccaattat     180
tcactgactt accacaggga aggagagaca ctcatgcatg aatgtccaga ctacataacc     240
ggtggcccca actcctgcca ctttggcaag cagtacacct ccatgtggag gacatacatc     300
atgatggtca atgccactaa ccagatggga agcagtttct cggatgaact ttatgtggac     360
gtgacttaca tagttcagcc agaccctcct ttggagctgg ctgtggaagt aaaacagcca     420
gaagacagaa acccctacct gtggattaaa tggtctccac ctaccctgat tgacttaaaa     480
actggttggt tcacgctcct gtatgaaatt cgattaaaac cgagaaagc  agctgagtgg     540 gagatccatt ttgctgggca gcaaacagag tttaagattc tcagcctaca tccaggacag     600
aaataccttg tccaggttcg ctgcaaacca gac                                   633
```